(12) United States Patent
Hineno et al.

(10) Patent No.: US 6,207,174 B1
(45) Date of Patent: Mar. 27, 2001

(54) COMPOSITE POWDER AND COLORING CONTAINING THE SAME

(75) Inventors: Teruhiko Hineno; Asa Kimura, both of Kanagawa (JP)

(73) Assignee: Shiseido Company, Ltd., Tokyo (JP)

( * ) Notice: Subject to any disclaimer, the term of this patent is extended or adjusted under 35 U.S.C. 154(b) by 0 days.

(21) Appl. No.: 09/200,969

(22) Filed: Nov. 30, 1998

(30) Foreign Application Priority Data

Dec. 1, 1997 (JP) .................................................... 9-345885
Nov. 6, 1998 (JP) .................................................. 10-316105

(51) Int. Cl.[7] .............................. A61K 6/00; A61K 7/00; A61K 31/74
(52) U.S. Cl. ....................................... 424/401; 424/78.03
(58) Field of Search .......................... 514/951; 424/401, 424/78.03

(56) References Cited

U.S. PATENT DOCUMENTS

| | | | |
|---|---|---|---|
| 5,122,418 | * 6/1992 | Nakane et al. | 424/401 |
| 5,165,915 | * 11/1992 | Tokubo et al. | 424/63 |
| 5,182,103 | * 1/1993 | Nakane et al. | 424/78.03 |
| 5,714,526 | * 2/1998 | Whyzmuzis | 523/161 |
| 5,856,377 | * 1/1999 | Sato et al. | 523/201 |

FOREIGN PATENT DOCUMENTS 0913432A   5/1999  (DE) .

OTHER PUBLICATIONS

Database WPI, Mar. 26, 1998, Abstract & WO 98 11865 A.
Database WPI, Jun. 18, 1998, Abstract & WO 98 26011A.
Patent Abstracts of Japan, Mar. 3, 1998, vol. 1998, No. 08, Abstract.
Japanese Patent Publication (Laid–Open) No.: 61–57653, Publication Date, Mar. 24, 1986.
Japanese Patent Application No. 59–180146, Filing Date, Aug. 28, 1984 and Partial Translation.

* cited by examiner

Primary Examiner—Thurman K. Page
Assistant Examiner—S. Howard
(74) Attorney, Agent, or Firm—Townsend & Banta

(57) ABSTRACT

Provided are a composite powder comprising a core particle which is spherical and has a refractive index of from 1.40 to 1.60, and a coating component which is coated on the surface of the core particle in film form and has a refractive index of from 2.00 to 2.90, and a coloring composition containing the composite powder. The composite powder or coloring composition is coated on a coating surface to form a composite powder layer. The composite powder layer causes light interference to exhibit a color on the surface. The composite powder and coloring composition are used in various fields.

20 Claims, 3 Drawing Sheets

COMPOSITE POWDER AND COLORING CONTAINING THE SAME

BACKGROUND OF THE INVENTION

1. Field of the Invention

The present invention relates to a composite powder and a composition containing this composite powder. More specifically, the present invention relates to a composite powder which can give a desired color by light interference and a coloring composition comprising the same.

2. Description of Related Art

A color is a quite important element which can give us a physiological influence or a psychological influence. Actually, a color conditioning technology which creates a safe efficient working environment or a healthy comfortable living environment using a physiological or psychological effect that a color can give us has been used in various fields.

Usually, when a product is colored, various color pigments are employed. The color pigments are those for applying a fixed color to a product utilizing a phenomenon of light absorption or scattering.

However, it is difficult to meet various requirements for colors these days with only the color pigments.

Accordingly, a pearlescent pigment such as titanium dioxide-coated mica or the like, which is a pigment with the use of a phenomenon of light interference, is provided in addition to the above-mentioned color pigments. The great characteristic feature of the pearlescent pigment is that a "flip-flop effect" by which a color is delicately changed according to an angle can be imparted to a product obtained by using the same.

This pearlescent pigment has currently been used in various fields such as cosmetics and the like.

However, pearlescent pigments which are currently used are not necessarily free from defects.

For example, with respect to an ordinary pearlescent pigment which is used as a pigment of an external composition such as cosmetics or the like, various approaches have been attempted on the color. However, particles thereof are laminar or flaky, and cosmetics containing the same lack smoothness. Thus, the pearlescent pigment is problematic in the use. Further, since a gloss of the ordinary pearlescent pigment is generally quite strong, it is unavoidable that the amount thereof in cosmetics tends to be limited.

In one aspect, the problems attendant on the use and the excessive gloss can be solved by making the particles of the pearlescent pigment spherical. However, since the spherical particles have a great light scattering property, it is quite difficult to create a color by interference.

The problem to be solved by the present invention is to provide a novel composite powder which does not have the defects of such a conventional pearlescent pigment and by which a color can be created by interference, and to provide means for using the powder in various fields.

SUMMARY OF THE INVENTION

The present inventor has assiduously conducted investigations to solve this problem, and have consequently solved the problem by providing a composite powder comprising a core particle which is spherical and a coating component coated the surface of the core particle, having a specific relationship between the core particle and the coating component, and by using the composite powder, the particles of which have a uniform particle diameter.

That is, the present inventors provide the following inventions in the present application.

The present invention first provides a composite powder comprising a core particle which is spherical and has a refractive index of from 1.40 to 1.60, and a coating component which is coated on the surface of the core particle in film form and has a refractive index of from 2.00 to 2.90.

Further, the present invention provides the above-mentioned composite powder wherein the coating component coated on the surface of the spherical particle in film form has an optical film thickness between 190 and 780 nm.

Still further, the present invention provides the above-mentioned composite powder wherein the core particle is silicon dioxide, and the coating component is titanium dioxide.

Furthermore, the present invention provides a method of use of the above-mentioned composite powder wherein the composite powder, the particles of which have a uniform particle diameter, is coated on a coating surface to form a composite powder layer on the coating surface, and light interference is caused in the composite powder layer whereby the composite powder layer exhibits a color on the coated surface.

Moreover, the present invention provides a "coloring composition" containing the above-mentioned composite powder, the particles of which have a uniform particle diameter, as a coloring component. This "coloring composition" includes various compositions, for example, an external composition such as makeup products or the like, a paint composition, a printing ink composition and a sticky composition.

Still moreover, the present invention provides a method of use of the coloring composition wherein the coloring composition is coated on a coating surface to form a composite powder layer on the coating surface and light interference is caused in the composite powder layer whereby the composite powder layer exhibits a color on the coating surface.

That is, the present invention provides a multi-purpose composite powder which can be used in various fields owing to the interference color, and a coloring composition for coloring an object using the interference color of this composite powder. This coloring composition can include the various types of composition, for example, an external composition such as makeup products or the like, a paint composition, a printing ink composition, a sticky composition and the like.

Further, the present invention provides a method of use of the composite powder or the coloring composition for most exhibiting the function of the above-mentioned composite powder or coloring composition.

DETAILED DESCRIPTION OF THE INVENTION

Figure 1A:
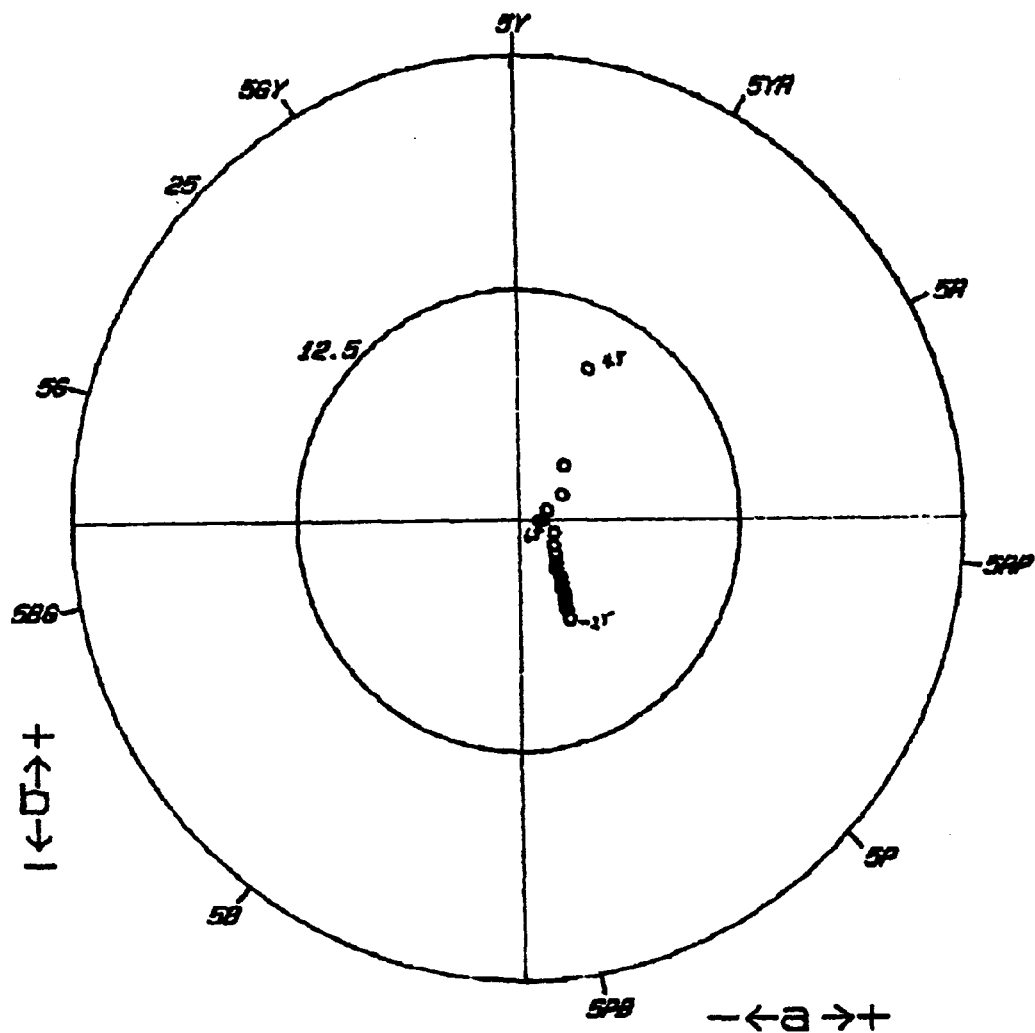
FIGS. 1A–1C are views showing the results of measuring the change of light according to an angle in a cream of Example 1 containing the composite powder of the present invention, and creams of Comparative Examples 1 and 2, using a spectrophotometer.

The present invention is described below in detail.

A. Composite powder the present invention

The composite powder of the present invention is a composite powder of which the core particle is spherical. The composite powder of the present invention, the particles of which have a uniform particle diameter, is coated on a coating surface to form a composite powder layer on the coating surface and light interference is caused in the composite powder layer, whereby the composite powder layer exhibits a color on the coating surface. In the composite powder of the present invention, a substance having a specific refractive index is coated to a specific thickness on the core particle, whereby the directly reflected light of the coating substance and the reflected light which is entered into the coating layer and reflected by the core particle interfere with each other, and a specific interference color is observed owing to a difference between phases thereof.

The great characteristic feature of the composite powder of the present invention is that the particles thereof are spherical, while the particles of the conventional light interference powder are flaky.

The core particle of the composite powder of the present invention is a so-called spherical particle. The spherical particle can be produced by known methods. For example, the spherical particle can be produced using a centrifugal rotation-type powder coating device (for example, a CF-granulated).

For example, when a starting material as a core of the spherical particle is charged into a CF-granulator, a rotor is rotated at high speed, and the powder is centrifugally rotated in doughnut form along an inner wall of a stator as if a rope is made. And while a binder solution or a coating solution is sprayed on the powder which is being centrifugally rotated, a coating powder is scattered thereon. Consequently, the core is coated with the coating powder, making it possible to make the particle spherical.

Further, a commercially available spherical powder (a commercially available powder composed of spherical particles) can also be used as the core particle of the composite powder of the present invention.

With respect to the property of the above-mentioned core particle, the refractive index has to be between 1.40 and 1.60. When the refractive index is less than 1.40 or exceeds 1.60, a desired interference color can hardly be obtained even if the following coating component is coated on the surface of the core particle, this being undesirous.

Specific examples of the material of the core particle having this range of the refractive index include silicon dioxide, alumina, calcium carbonate, barium sulfate, nylon, polyethylene, polystyrene and polymethyl methacrylate. Of these, silicon dioxide is a material which is preferably selected as a material of the core particle in view of the facts that it is relatively easy to control its shape and the uniformness of the surface and that it is also relatively easy to form a uniform interference coating on the surface thereof. The particle diameter of the core particle is preferably between 2.0 $\mu$m and 50.0 $\mu$m. When this particle diameter is less than 2.0 $\mu$m, the light scattering is excessively increased, and a desired interference color is hardly obtained even if the following coating component is coated on the surfaces of the core particles, this being undesirous. When it exceeds 50.0 $\mu$m, the usability of an external composition into which the composite powder of the present invention is incorporated is decreased, this being undesirous.

The composite powder of the present invention can be formed by coating a coating component having a refractive index of from 2.00 to 2.90 in film form on the core particle.

The fact that the refractive index of this coating component is in the above-mentioned range corresponds to the fact that the material of the core particle is one having the above-mentioned range of the refractive index.

That is, when the refractive index of the coating component deviates from the above-mentioned range, it is difficult to obtain a desired interference color, this being undesirous.

Examples of the coating component having the above-mentioned refractive index include titanium dioxide, specific lower titanium oxide (titanium oxide having a lower rate of titanium oxidation than titanium dioxide, for example, $Ti_2O$, $TiO$, $Ti_2O_3$, $Ti_3O_5$ and $Ti_4O_7$), zinc oxide, zirconium oxide and iron oxide.

Of these coating components, titanium dioxide is a material which is preferably selected as a coating component in that it is relatively easy to form the coating on the surface of the core particle.

A method of coating the coating component on the core particle is not particularly limited so long as the coating component can be coated on the surface of the core particle in uniform film form, and known coating methods can be employed.

For example, when titanium dioxide is selected as a coating component, a method in which hydrous titanium dioxide is precipitated on a surface of a core particle in an aqueous solution of a titanium inorganic acid salt (for example, titanyl sulfate) and then heated in an ambient atmosphere, and a method in which while a titanium alkoxide is contacted with a core particle in a solvent, this titanium alkoxide is hydrolyzed and burned, can be used.

Further, when lower titanium oxide is selected as a coating component, for example, a method in which the composite powder of the present invention coated with titanium dioxide as prepared above is heated and reduced at from 500 to 1,000° C., preferably at from 700 to 900° C. using a gas having a reducing power, such as a hydrogen gas or an ammonia gas, a mixed gas of the gas having the reducing power and an inert gas such as a helium gas, an argon gas or a nitrogen gas, or a reductive flame of hydrogen or the like, and a method in which metallic titanium or silicon dioxide and the composite powder of the present invention already coated with titanium dioxide are mixed, and heated and reduced at from 700 to 900° C., can be used.

The thickness of the coating layer of the above-mentioned coating component in the composite powder of the present invention in which the core particle is coated with the coating component can be selected, as required, according to the type of the interference color imparted to the composite powder of the present invention and the type (refractive index) of the material selected as the core particle or the coating component.

The thickness of the coating layer in the composite powder of the present invention is an optical film thickness (film thickness×refractive index), and it is advisable that the thickness of the coating layer is approximately selected in the range of from 190 to 780 nm (when the coating component is titanium dioxide and the core particle is formed of silicon dioxide, the coating component/core particle weight ratio is approximately in the range of from 0.09 to 1.25, preferably in the range of from 0.4 to 1.0). When the thickness of the coating layer is too low (the coating component/core particle weight ratio is less than 0.09 in the above-mentioned example), it is hard to give a desired interference color, this being undesirous. Meanwhile, when the thickness of the coating layer is too high (the coating component/core particle weight ratio exceeds 1.25 in the above-mentioned example), the coating component is not uniformly coated on the core particle, decreasing an intensity of an interference color, this being undesirous.

For reference, the relationship of the interference color when the composite powder of the present invention is coated on a substrate and the optical film thickness expected of titanium dioxide coated on the core particle is shown in Table 1 below.

As will be later described, in the composite powder of the present invention, an interference color is scarcely observed with the particle alone. The results provided when observing the interference color of the coating of the composite powder, the particles of which have a uniform particle diameter, are shown in Table 1.

Specifically, 1 g of the composite powder of the present invention having each of various coating component (titanium dioxide)/core particle (silicon dioxide) weight ratios was dispersed in a nitrocellulose lacquer, and a film was formed to a thickness of 0.1 mm using an applicator. An interference color in this film was observed, and an optical film thickness expected was calculated. The results are shown in Table 1.

TABLE 1

| Interference Color | Optical Film Thickness (nm) |
|---|---|
| Yellow | 210 |
| Red - Reddish purple | 290 |
| Blue | 330 |
| Green | 395 |
| Yellow | 425 |
| Red - Reddish purple | 550 |
| Blue | 590 |
| Green | 630 |

It is advisable that the particle diameter of the composite powder particles in the present invention is as uniform as possible.

That is, in each of spherical particles of a composite powder, it is hard to obtain a desired interference color by scattered light. Meanwhile, when the composite powder in which the particle diameters of the particles are uniform to some extent is coated on an object, the coating component and the core particles are arranged on the surface of the object as if the coating component is coated thereon in layered form as an upper layer, making it possible to obtain a desired interference color.

Thus, it is advisable for fully exhibiting the predetermined effect of the present invention that the particle diameter of the particles of the composite powder in the present invention is uniform as much as possible to maintain the uniformness of the coating surface as much as possible.

In the present invention, the condition in which "the particles of the composite powder have a uniform particle diameter" or "the particle diameters of the particles of the composite powder are uniform" means that in the measurement with a particle diameter distribution meter in a laser diffraction scattering method, a Coulter method or the like, the particle diameters of the particles of the powder are distributed at a ratio of 60% or more, preferably 70% or more in terms of a volume distribution within the range of (X±3) μm wherein X μm is an average particle diameter of the particles of the powder.

In order to maintain the uniformness of the particle diameter, it is advisable to carefully conduct "screening" in producing the core particle. When a commercially available product is selected as the core particle of the composite powder, it is advisable to select a product having an excellent uniformness of the particle diameter.

Further, in view of obtaining as uniform an interference color as possible, it is advisable that the surface of the core particle is as smooth and flat as possible.

In this manner, the desired composite powder of the present invention can be obtained.

The composite powder of the present invention is uniformly coated on a coating surface. When light is applied thereto, the reflected light from the surface of the coating component located on the upper layer of the coating surface and the reflected light which is entered into the coating component and reflected on the core particle interfere with each other, and a specific interference color is observed.

This interference color mainly depends on the refractive index of the core particle, the refractive index of the coating component and the film thickness of the coating component in the composite powder of the present invention as mentioned above. That is, the desired interference color can be obtained from the composite powder of the present invention by properly adjusting these factors determining the interference color.

And the particles of the composite powder of the present invention are spherical unlike titanium mica which is a conventional composite powder, whereby the usability in using the coloring composition (which will be later described) containing the composite powder of the present invention as an external composition can abruptly be improved.

The composite powder of the present invention having the quite excellent characteristics as mentioned above is extremely excellent as a component of the "coloring composition" which mainly serves to color an object.

B. Coloring composition of the present invention

As stated above, the "coloring composition" of the present invention is a composition which mainly conducts coloration of an object (the concept of this "coloration" includes not only coloration with the above-mentioned "color pigment", but also impartation of an interference color using light interference). Its specific mode is not particularly limited. Examples thereof include an external composition such as a makeup product or the like, a paint composition, a printing ink composition and a sticky composition.

The coloring composition of the present invention contains the composite powder of the present invention as an essential component. When the coloring composition of the present invention is coated on an object, the object is colored by the interference color in the composite powder of the present invention.

That is, the coloring composition of the present invention is coated on the coating surface, and light interference can be caused in the composite powder layer formed on the coating surface, so that the composite powder layer exhibits a color on the coating surface.

The content of the composite powder in the coloring composition of the present invention can be selected, as required, depending on a specific type, a purpose or the like of the composition, and it should not be particularly limited.

Typical types which the coloring composition of the present invention can take are described below.

(1) When the coloring composition of the present invention is an external composition:

In the external composition such as cosmetics or the like, a role of especially a makeup product includes a "beautiful role" by which a person looks beautiful, a "protective role" by which to protect the skin, and a "psychological role" by which to give a refreshed feeling.

In order to play these roles satisfactorily, it is inevitable to improve the color requirement of the makeup product and the usability.

As a component that plays a main role in the makeup product, a powder component is taken up. In the powder component, especially a pigment component gives a color to the makeup product, and it further plays the above-mentioned "protective role" upon exhibiting a ultraviolet-screening effect or the like depending on the type thereof.

Accordingly, the main problems in producing excellent makeup products are that the color requirement of the pigment component is improved and the requirement directly related with the usability of the beauty product is improved.

The pigment component includes a component which gives a specific color to a makeup product by absorption and scattering of light, and a "light interference powder component" that gives further various colors by interference. For example, a pearlescent pigment typified by mica titanium can give pearlescence, iris or a metallic feeling by the interference color to a makeup product by incorporating the same therein.

That is, in the pearlescent pigment, laminar particles are arranged regularly in parallel in an colored product to reflect light, and the reflected light causes interference to be able to give pearlescence.

And various approaches were made on this interference color, and a composite powder which gives not only pearlescence but also various colors required is currently being provided.

However, when the composite powder which is currently provided is used in an external composition typified by the makeup product, the problems such as a usability, an excessively strong gloss and the like are found as stated above.

The present invention has succeeded in solving the problems by using the above-mentioned coloring composition of the present invention as an external composition.

That is, the present invention provides an external composition containing the composite powder of the present invention (hereinafter referred to also as an "external composition of the present invention").

The external composition having various colors and exhibiting the abruptly improved usability is provided by incorporating the composite powder of the present invention therein.

The content of the composite powder in the external composition of the present invention can be selected, as required, depending on the form or the type of the composition, the purpose of incorporating the composite powder of the present invention and the like, and it shall not particularly be limited. It is usually incorporated in the range of from 0.1 to 90.0% by weight based on the overall composition.

Further, the external composition of the present invention can contain other components which are ordinarily incorporated in cosmetics unless predetermined effects of the present invention are impaired.

For example, a solid or semisolid oil such as vaseline, lanolin, ceresin, carnauba wax, candelilla wax, a higher fatty acid or a higher alcohol, a liquid oil such as squalane, a liquid paraffin, an ester oil or triglyceride, an oil such as a silicone oil, a moisturizer such as sodium hyaluronate or glycerin, a surface active agent such as a cationic surface active agent or a nonionic surface active agent, a pigment, a preservative, a perfume, an activator, and an ultraviolet-screening agent can be incorporated as required.

The external composition of the present invention can take a form such as a powder, a cake, a pencil, a stick, an ointment, a liquid or the like. The external composition of the present invention can be applied to a facial product such as a lotion, an emulsion or a cream; a makeup product such as a foundation, a lipstick, an eye shadow, a rouge, an eye liner, a nail enamel or a mascara; and a haircare product such as a hair treatment, a hair liquid or a set lotion. When the external composition of the present invention is a makeup product, the excellent characteristics of the composite powder of the present invention can be most exhibited.

The external composition of the present invention is coated on the skin as the coating surface, and the light interference is caused in the composite powder layer having the uniform particle diameter formed on the skin, so that the composite powder layer exhibits a color on the skin and various interference colors are observed. Further, since the particles of the composite powder are spherical, the usability is much improved compared with the conventional pearlescent pigment.

The specific formulation of the external composition of the present invention is mentioned in Examples to be described later.

(2) When the coloring composition of the present invention is a paint composition (hereinafter referred to as a "paint composition of the present invention"):

When a product is colored, a color "paint composition" is used in many cases. The paint composition is a composition which has first a fluidity, is adhered to a surface of a product by being coated thereon, and then forms a continual film on the surface through a drying step.

Such a color paint composition contains a pigment for coloring a product. It often contained the above-mentioned color pigment in the past.

However, at present, it is required to apply various colors to a product, and the pigment is required to be a pearlescent pigment which can exhibit the above-mentioned flip-flop effect and various interference colors.

The composite powder of the present invention is excellent as a pigment of a paint composition in that the various interference colors are given to the product as mentioned above, and further the particles are spherical. Accordingly, the paint composition containing the composite powder of the present invention as a pigment is also excellent in that the unevenness of coating can effectively be prevented.

Thus, the present invention also provides the paint composition as the above-mentioned coloring composition.

The paint composition of the present invention contains the composite powder of the present invention as the pigment, as stated above. The content of the composite powder in the paint composition of the present invention can be selected, as required, depending on the specific type, purpose or the like of the paint composition, and it is not limited at all. Especially, the composite powder of the present invention is composed of spherical particles, so that even when it is incorporated in a larger amount than the conventional pearlescent pigment, it is easily coated uniformly on a product and the unevenness of coating or the like can be prevented.

The paint composition of the present invention can contain elements which are usually incorporated in a paint composition unless the predetermined effects of the present invention are impaired.

Specifically, the paint composition of the present invention can contain film-forming main elements such as a polymeric oil, a natural or synthetic resin, and a high-molecular substance, for example, cellulose and rubber derivatives; film-forming auxiliaries such as a plasticizer, a drying agent, a curing agent, an anti-skinning agent, a fluidity modifier (a tackifier, a flattening agent or the like), an anti-sagging agent, a preservative, a mildew proofing agent, a rust-proofing agent and an ultraviolet absorber; and a pigment, other than the composite powder of the present invention.

A solvent for solving the above-mentioned film-forming elements can selectively be used as required.

In the paint composition of the present invention, the light interference is caused in the composite powder layer having the uniform particle diameter formed on the coating surface so that the composite powder layer exhibits a color on the coating surface, whereby the various interference colors are observed.

The paint composition of the present invention can widely be used as various paints such as a building paint, a stone paint, a vehicle paint, a ship paint, a ship bottom paint, a wood paint, an equipment paint, a mark paint, an electric insulation paint, an electroconductive or semiconductive paint, a chemical-resistant paint, an anti-corrosive paint, a heat-resistant paint, a fire-resistant paint, a temperature indicating paint, a luminous paint and an insecticidal paint.

The specific formulation of the paint composition of the present invention is mentioned in Examples to be described later.

(3) When the coloring composition of the present invention is a printing ink composition (hereinafter referred to as a "printing ink composition of the present invention):

The printing ink composition is a composition which is used as an image-forming material for forming and fixing an image defined in a manuscript, a print or the like on a surface of a product to be printed through printing.

This printing ink composition is different from the above-mentioned paint composition in that it has a "printability" which is required for producing a printed matter without trouble in a printing step.

In such a printing composition, a coloring material such as a pigment, a dye or the like is also incorporated, and the above-mentioned color pigment was used as the coloring material in many cases.

However, since there is a need to provide more colorful printing, the use of a pearlescent pigment as a coloring material has been studied as in the above-mentioned paint composition.

The composite powder of the present invention is excellent as a coloring material in a printing ink composition in that various interference colors are applied to a product. Furthermore, the composite powder of the present invention is composed of spherical particles. Accordingly, it is also excellent in that the unevenness of printing can effectively be prevented in a printed matter provided by using the printing ink composition containing this composite powder as a coloring material.

Thus, the present invention also provides a printing ink composition as the above-mentioned coloring composition.

The printing ink composition of the present invention contains the composite powder of the present invention as the coloring material as mentioned above. The content of the composite powder in the printing ink composition of the present invention can be selected, as required, depending on the printability required from the specific type, purpose or the like of the printing ink composition of the present invention, and it is not limited at all. Especially, since the composite powder of the present invention is composed of spherical particles, even if a larger amount thereof is incorporated in comparison with the conventional pearlescent pigment, the printing ink composition of the present invention can easily be adhered to a product more uniformly, making it possible to prevent the unevenness of printing or the like.

The printing ink composition of the present invention can contain, other than the composite powder of the present invention, elements which can usually be added to a printing ink composition unless the predetermined effects of the present invention are impaired.

Specifically, the printing ink composition of the present invention can contain a coloring material such as a pigment or a dye other than the composite powder of the present invention; a vehicle such as an oil (a vegetable oil such as a linseed oil, a tung oil or the like, or a mineral oil such as an ink oil or a solvent); a resin (a natural resin such as gilsonite or rosin, or a synthetic resin such as a rosin-modified phenolic resin, amaleic acid resin, apetroleum resin, an alkyd resin or an ester gum), a plasticizer, a wax or a solvent; an aid such as a drying controlling agent (a dryer or an anti-skinning agent), a viscosity modifier (a compound, a tackifier or a buckling agent), a dispersibility controlling agent (a dispersant, a segregation preventing agent or a stabilizer), a color adjustor (a toner or a delustering agent), a reactant (a photopolymerization initiator, a catalyst or a crosslinking agent); a wetting agent; a defoamer; and a mildewproofing agent.

In the printing ink composition of the present invention, the light interference is caused in the composite powder layer having a uniform particle diameter formed on the coating surface and then subjected to the printing step, so that the composite powder layer exhibits a color on the coating surface, whereby the various interference colors are observed.

Thus, the printing ink composition of the present invention can widely be used as various printing inks, for example, a litho printing ink, a gravure printing ink, a letterpress printing ink, a screen printing ink, a flexographic printing ink, an intaglio printing ink or various special printing inks.

The specific formulation of the printing ink composition of the present invention is mentioned in Examples to be described later.

(4) When the coloring composition of the present invention is a sticky composition (hereinafter referred to as a "sticky composition of the present invention"):

The sticky composition refers to a composition which is itself sticky. Specifically, the sticky composition is used, for example, as a tackifier of a sticky sheet for decoration. Especially in the present invention, in order to color a product to which the sticky sheet for decoration is stuck and stick the sticky sheet on the product, the above-mentioned sticky composition is used by being coated on at least one surface of such a sticky sheet.

Heretofore, in a sticky sheet, a layer in which a tackifier layer obtained by coating a coloring sticky composition on both surfaces or one surface of a substrate of a sheet as a support is laminated with a peel-off liner layer is formed. When the sticky sheet is used, the peel-off liner layer is peeled off, and the sticky sheet is stuck on a product (of various materials) to be stuck, so that the stuck product is decorated with a color, a pattern, a metal luster or the like to give designing.

However, in the coloring sticky composition which has been so far used, the above-mentioned color pigment is employed as a coloring means. Therefore, it could not be denied that in its use, the change in the color typified by the above-mentioned flip-flop effect is poor and the adhesion tends to be considered more important than the coloring function.

Accordingly, it has been required at present to provide means which can impart an interference color capable of exhibiting the flip-flop effect to the above-mentioned sticky sheet or the like.

The present invention provides the sticky composition in which the composite powder of the present invention is used as a color pigment in the coloring sticky composition used in this sticky sheet whereby various interference colors having the above-mentioned flip-flop effect and the like can be applied to the stickysheet. As described above, the composite powder of the present invention can provide the various interference colors and is further composed of spherical particles, with the result that the sticky composition of the present invention can advantageously be coated on the sticky sheet easily without unevenness.

Thus, the present invention provides the sticky composition as the coloring composition.

The sticky composition of the present invention contains, as mentioned above, the composite powder of the present invention as the pigment. The content of the composite powder in the sticky composition of the present invention can be selected, as required, depending on the specific type, purpose or the like of the sticky composition, and it is not limited at all. However, in order to impart the flip-flop effect to the sticky sheet obtained by using the sticky composition of the present invention, it is advisable to contain the composite powder of the present invention in an amount of at least 1.0% by weight based on the composition.

The sticky composition of the present invention can contain, besides the composite powder of the present invention, elements which can ordinarily be added to a sticky composition unless the predetermined effects of the present invention are impaired.

Specifically, the sticky composition of the present invention is such a composition in which the composite powder of the present invention is incorporated into the tackifier. Such a tackifier can be selected, as required, from various tackifiers such as a rubbery tackifier (for example, natural rubbers, their derivatives, various synthetic rubbers or a mixture thereof), an acrylic tackifier (for example, a copolymer containing butyl acrylate or another acrylic monomer such as, typically, 2-ethylhexyl acrylate), a silicone tackifier (for example, a mixture of a silicone rubber and a resin), a polyether tackifier and a polyurethane tackifier. Further, a curing agent, various coloring agents and pigments, other than the composite powder of the present invention, can also be incorporated therein.

The specific formulation of the sticky composition of the present invention is mentioned in Examples to be described later.

As stated above, the sticky composition of the present invention is used in, for example, the sticky sheet. In this case, it is possible that the sticky composition of the present invention is coated on the support layer of the sheet and the peel-off liner layer is formed on the upper surface thereof.

As the support of the sticky sheet, a known material which can be used as a support of the sticky sheet can be employed. Examples thereof include sheets of plastics such as polyester, polyvinyl chloride, polycarbonate, polyethylene, polypropylene, nylon, polystyrene, an ethylene-vinyl acetate copolymer and the like, and glass plates.

The support of the sticky sheet previously printed can be also used. In such a printing, the above-mentioned printing ink composition of the present invention may be used.

As the peel-off liner layer, a peel-off liner layer which has ordinarily been used can be employed. For example, paper, a plastic film or the like is available, and it can be selected, as required, depending on the use of the sticky sheet.

In this sticky sheet, the light interference can be caused in the composite powder layer of the present invention formed by coating the sticky composition of the present invention, so that the composite powder layer exhibits a color.

Thus, the coloring composition of the present invention includes many types. However, the type of the coloring composition of the present invention is not limited to the above-mentioned. For example, a "plastic coloring product" obtained by kneading a resin with the composite powder of the present invention, as will be described later in Examples, is also the coloring composition of the present invention.

C. The composite powder of the present invention can improve qualities of a liquid crystal display using a liquid crystal display diffusion plate by incorporating the same into this diffusion plate.

That is, a liquid crystal display containing the composite powder of the present invention as uniformly as possible, by adjusting the wavelength of the interference light obtained by the composite powder of the present invention so as to be identical with the absorption length of light in the liquid crystal display diffusion plate, efficiently uses light from a back light without interruption by the light absorption of the diffusion plate, making it possible to save an electric power.

The liquid crystal display diffusion plate containing the composite powder of the present invention is commonly used as a film formed of a layer of a resin having a transparent color, such as nitrocellulose, an acrylic polymer, polycarbonate, polyester or polyurethane, this film having a film thickness of from 10 to 500 $\mu$m.

The composite powder of the present invention is contained in the above-mentioned resin material as uniformly as possible, and the mixture is molded into a film, or the resin material is uniformly coated on a substrate of a transparent color, whereby a desired liquid crystal display diffusion plate can be obtained.

The content of the composite powder of the present invention in this liquid crystal display diffusion plate is preferably in the range of from approximately 1 to 70% by weight based on the overall diffusion plate.

By using this liquid crystal display diffusion plate, a light flux entered from a light source is uniformly diffused on the display, and light of a specific wavelength which is lost by light absorption of the diffusion plate itself in the incidence is supplemented by the interference light of the specific wavelength which is generated in the composite powder of the present invention contained in such a diffusion plate, making it possible to effectively utilize light from the light source and provide a clear beautiful image.

The above-mentioned diffusion plate can contain a white pigment such as titanium dioxide mica, barium sulfate, zinc oxide, magnesium oxide or the like to give a well-balanced color.

The liquid crystal display in which this liquid crystal display diffusion plate is used is not particularly limited. It can be used in various liquid crystal displays, for example, a TN-type liquid crystal display, an STN-type liquid crystal display, a DSTN-type liquid crystal display, an F-STN-type liquid crystal display, a CSH-type display and a ferroelectric liquid crystal display, and various illuminations.

The present invention is illustrated m ore specifically by referring to the following Examples. However, the technical scope of the present invention is not limited by these Examples.

The amount in Examples is parts by weight unless otherwise instructed.

The (L* a* b*) value shown in Production Examples and the like was measured by the following method:

One gram of the composite powder of the present invention was dispersed in 15 g of a nitrocellulose lacquer, and the dispersion was coated on a black paper to a film thickness of 0.101 mm. The change of light according to an angle was measured using a varied-angle spectrophotometer supplied by Murakami Shikizai, and the (L* a* b*) value at an incident angle of 45° and a light reception angle of −25° was shown.

PRODUCTION EXAMPLES

Production of a composite powder of the present invention (1)

Commercially available spherical silicon dioxide (particle diameter: 5.62 μm, refractive index: 1.46) and tetraisopropoxy titanium were dispersed into isopropanol, and an aqueous ethanol solution was gradually added dropwise to the dispersion. At this time, the amount of tetraisopropoxy titanium was adjusted such that the amount of titanium dioxide reached 80 parts per 100 parts of spherical silicon dioxide.

After the completion of the dropwise addition of the aqueous ethanol solution, the product was filtered, then dried, and burned at 900° C. for 3 hours.

The resulting powder was pulverized to obtain spherical silicon dioxide coated with 80% titanium dioxide.

A light red interference color was observed in this composite powder of the present invention, and the (L* a* b*) value thereof was (21.76 9.85 −11.18) [In Examples, the composite powder produced in this example is designated Invention composite powder (1)].

Production of a composite powder of the present invention (2)

Spherical silicon dioxide coated with 100% titanium dioxide was obtained in the same manner as in (1) above except that the amount of tetraisopropoxy titanium was adjusted such that the amount of titanium dioxide reached 100 parts per 100 parts of the above-mentioned commercially available spherical silicon dioxide.

A green interference color was observed in the composite powder of the present invention, and the (L* a* b*) value thereof was (28.35 −6.09 −2.11) [In Examples, the composite powder produced in this example is designated Invention composite powder (2)].

Production of a composite powder of the present invention (3)

The above-mentioned commercially available spherical silicon dioxide was dispersed in water, and titanyl sulfate was heated in this dispersion at from 60 to 100° C. to conduct hydrolysis. At this time, the amount of titanyl sulfate was adjusted such that the amount of titanium dioxide reached 60 parts per 100 parts of spherical silicon dioxide.

This product was filtered, dried and burned at from 700 to 900° C. for 3 hours.

The resulting powder was pulverized to obtain spherical silicon dioxide coated with 60% titanium dioxide.

A pale yellow interference color was observed in the composite powder of the present invention, and the (L* a* b*) value thereof was (28.11 3.38 9.17) [In Examples, the composite powder produced in this example is designated Invention composite powder (3)].

Production of a composite powder of the present invention (4)

The above-mentioned commercially available spherical silicon dioxide was dispersed in water. An aqueous titanium tetrachloride solution was neutralized with an aqueous potassium hydroxide solution in this dispersion, and the titanium hydroxide precipitate was coated thereon. At this time, the amount of titanium tetrachloride was adjusted such that the amount of titanium dioxide reached 90 parts per 100 parts of spherical silicon dioxide.

This coated product was filtered, then dried, and burned at from 700 to 900° C. for 3 hours.

The resulting powder was pulverized to obtain spherical silicon dioxide coated with 60% titanium dioxide.

A pale blue interference color was observed in the composite powder of the present invention, and the (L* a* b*) value thereof was (23.37 0.68 −9.82) [In Examples, the composite powder produced in this example is designated Invention composite powder (4)].

These composite powder s of the present invention were used in the following Examples.

EXAMPLE 1

Cream:

| Components | Amount (parts by weight) |
|---|---|
| 1. Decamethylcyclopentasiloxane | 25.0 |
| 2. Polyether-modified silicone | 2.0 |
| 3. Bentonite | 2.0 |
| 4. Invention composite powder (1) | 5.0 |
| 5. 1,3-Butylene glycol | 10.0 |
| 6. Deionized water | 56.0 |
| 7. Paraben | suitable amount |
| 8. Antioxidant | suitable amount |
| 9. Perfume | suitable amount |

<Method>

A mixture of the above-mentioned components 4 to 7 was gradually added to a mixture of the above-mentioned components 1 to 3, 8 and 9 at 80° C. with stirring by a homodisper, and these were emulsified to obtain a desired cream.

(1) A cream of Comparative Example 1 was obtained in the above-mentioned manner except that the component 4 [Invention composite powder (1)] in the cream of Example 1 was replaced with a spherical silicon dioxide powder (used in the above-mentioned Production Examples).

(2) A cream of Comparative Example 2 was obtained in the above-mentioned manner except that the component (4) [Invention composite powder (1)] in the cream of Example 1 was removed and the amount of the component 1 (decamethylcyclopentasiloxane) was increased to 30.0 parts by weight.

Test of cosmetics a) Test using a spectrophotometer

Each of the creams of Example 1 and Comparative Examples 1 and 2 was coated on a black paper to a film thickness of 0.101 mm, and the change of light according to an angle was measured using a varied-angle spectrophotometer supplied by Murakami Shikizai.

This measurement was conducted upon fixing an incident angle at 45° and changing a light reception angle from −25° to 65°.

Figure 1B:
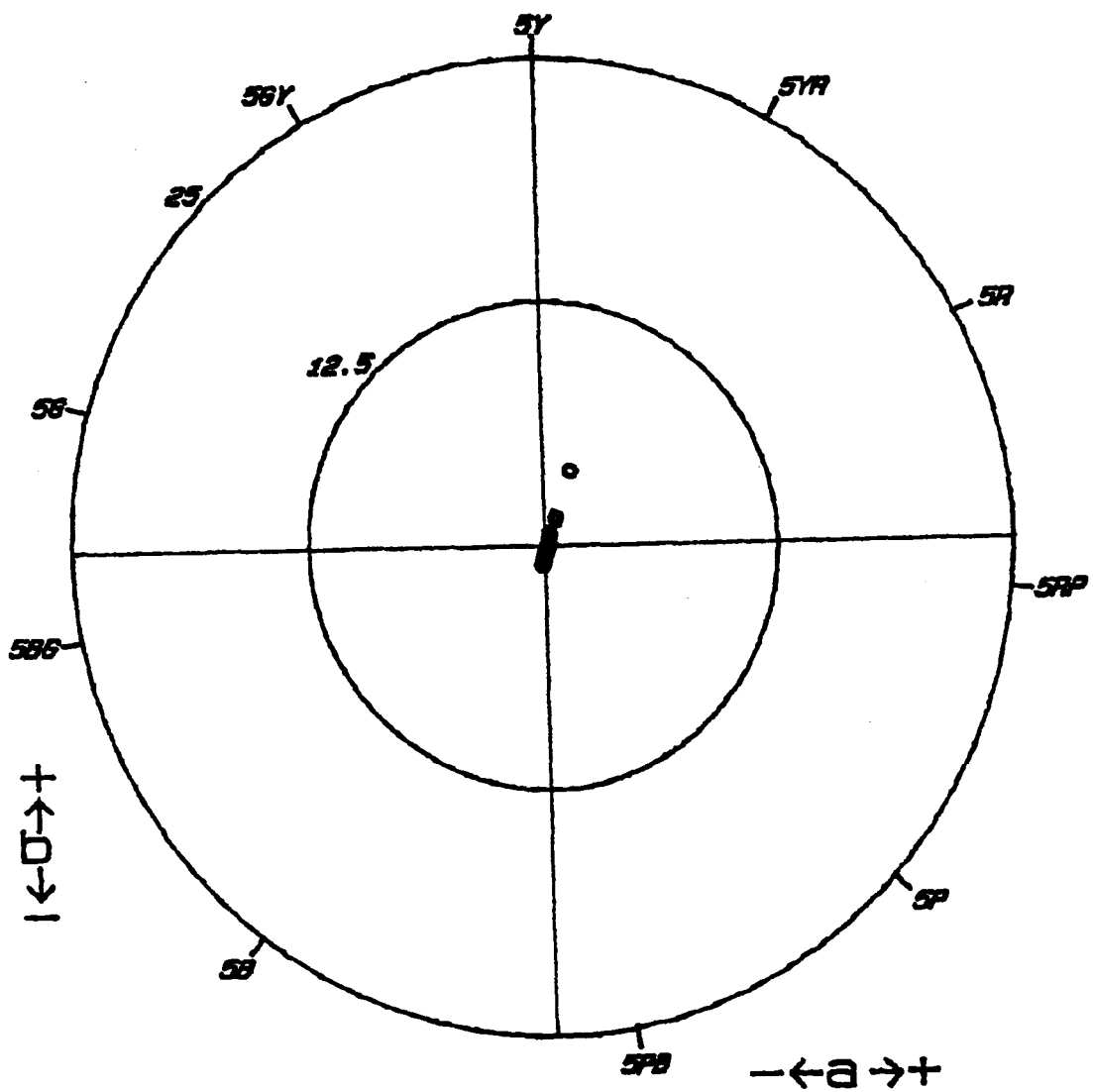
Figure 1C:
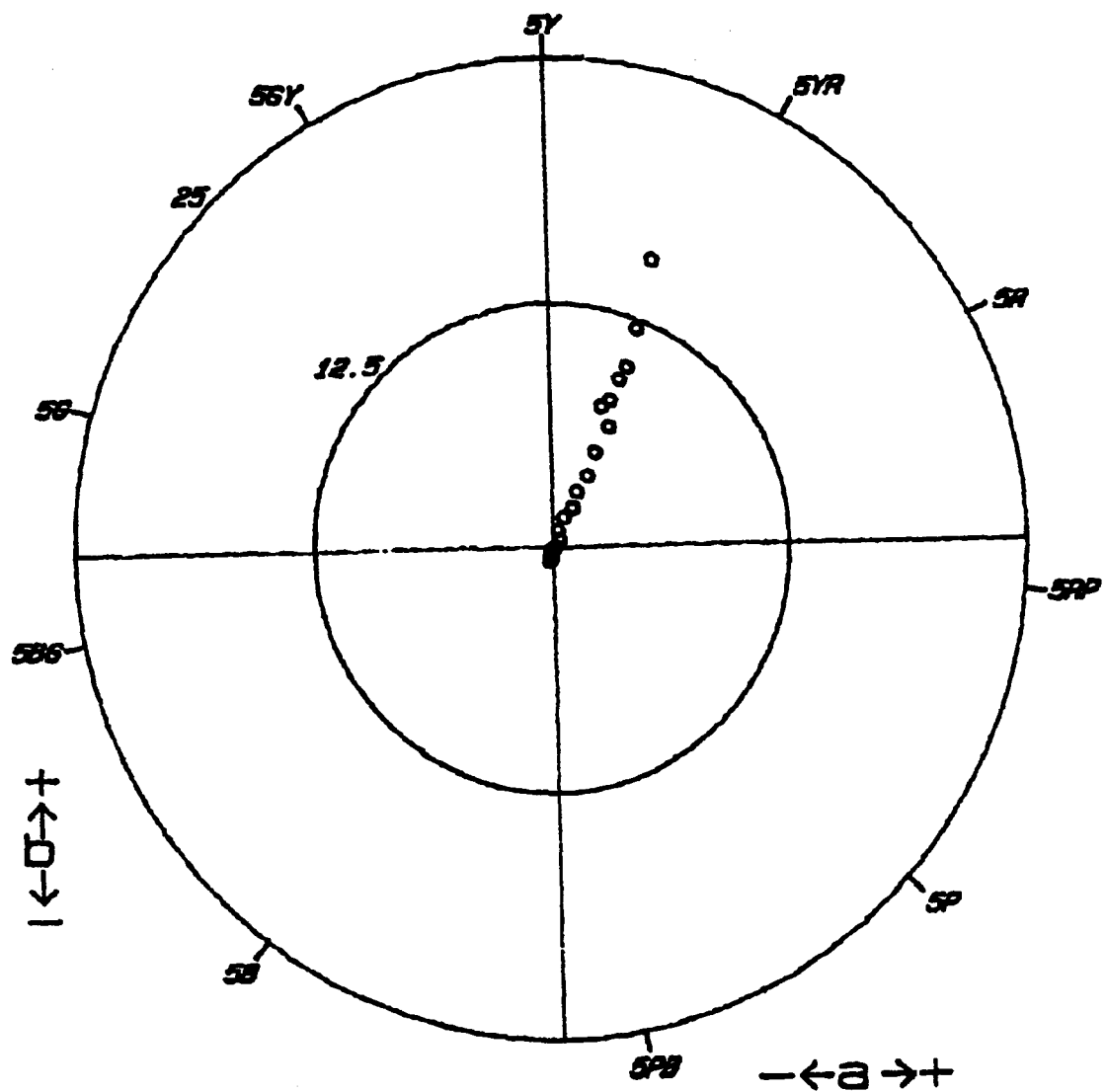

The results of this measurement are shown in FIGS. 1A–1C. FIG. 1A shows the results of the cream of Example 1, and FIGS. 1B–1C show the results of the creams of Comparative Examples 1 and 2. In these drawings, "Y" means yellow, "YR" means yellowish red, "R" means red, "RP" means reddish purple, "P" means purple, "PB" means purplish blue, "B" means blue, "BG"means bluish green, "G" means green, and "GY" means greenish yellow.

As shown in FIGS. 1B and 1C, no change of color was observed according to the change of angle in the creams of Comparative Examples 1 and 2. Meanwhile, as shown in FIG. 1A, in the cream of Example 1, the color was changed from reddish purple to red according to the change of angle. It was found that the interference color was generated.

b) Test for actual use

The test for actual use was conducted on the creams of Example 1 and Comparative Examples 1 and 2.

That is, each of these creams was evaluated by ten expert panelists on the items shown in Table 2 according to five scores 1 to 5. The average values were taken, and shown in Table 2 using the following marks.

⊚: at least 4.5 and at most 5.0
○: at least 3.5 and less than 4.5
Δ: at least 2.5 and less than 3.5
X: at least 1.5 and less than 2.5
XX: at least 1.0 and less than 1.5

TABLE 2

| Sample | Spreading in coating | Dry feeling After Coating | Effect of covering wrinkle | Effect of improving skin color after coating | Overall evaluation |
| --- | --- | --- | --- | --- | --- |
| Example 1 | ⊚ | ⊚ | ○ | ⊚ | ⊚ |
| Comparative Example 1 | ⊚ | ⊚ | Δ | X | ○ |
| Comparative Example 2 | X | XX | X | X | X |

This Table 2 revealed that the cream of Example 1 was not only excellent in the spreading in coating and the dry feeling after coating, but also had an effect of beautifully improving the skin color after coating.

EXAMPLE 2

Loose powder:

| Components | Amount (parts by weight) |
| --- | --- |
| 1. Invention composite powder (1) | 80.0 |
| 2. Kaolin | 5.0 |
| 3. Titanium dioxide powder | 3.0 |
| 4. Magnesium carbonate | 5.0 |
| 5. Sericite | 7.0 |
| 6. Perfume | suitable amount |

<Method>

The above-mentioned components 1 to 5 were mixed, and the perfume was sprayed thereon. These were uniformly mixed. The mixture was pulverized in a mill to obtain a desired loose powder.

(1) A loose powder of Comparative Example 3 was obtained in the above-mentioned manner except that the equal amount of a spherical silicon dioxide powder (used in the above-mentioned Production Examples) was used instead of the component 1 [Invention composite powder (1)] in the loose powder of Example 2.

(2) Further, a loose powder of Comparative Example 4 was obtained in the above-mentioned manner except that the equal amount of talc was used instead of the component 1 [Invention composite powder (1)] in the loose powder of Example 1.

Test of cosmetics
a) Test for actual use

The test for actual use was conducted with respect to the loose powders of Example 2 and Comparative Examples 3 and 4.

That is, each of these powders was evaluated by ten expert panelists on the items shown in Table 3 according to five scores 1 to 5. The average values were taken, and shown in Table 3 using the following marks.

⊚: at least 4.5 and at most 5.0
○: at least 3.5 and less than 4.5
Δ: at least 2.5 and less than 3.5
X: at least 1.5 and less than 2.5
XX: at least 1.0 and less than 1.5

TABLE 3

| Sample | Dry feeling after coating | Effect of covering wrinkle | Effect of improving skin color after coating | Overall evaluation |
| --- | --- | --- | --- | --- |
| Example 2 | ⊚ | ○ | ⊚ | ⊚ |
| Comparative Example 1 | ⊚ | Δ | X | ○ |
| Comparative Example 2 | XX | X | X | X |

This Table 3 revealed that the loose powder of Example 2 was not only excellent in the dry feeling, and especially excellent in the effect of improving the skin color after coating and the effect of covering wrinkle by the function of the interference color provided by the composite powder of the present invention.

EXAMPLE 3

Lip cream:

| Components | Amount (parts by weight) |
| --- | --- |
| 1. Invention composite powder (1) | 6.0 |
| 2. Candelilla wax | 9.0 |
| 3. Solid paraffin | 8.0 |
| 4. Bees wax | 5.0 |
| 5. Carnauba wax | 5.0 |
| 6. Lanolin | 11.0 |
| 7. Castor oil | 26.0 |
| 8. Cetyl 2-ethylhexanoate | 20.0 |
| 9. Isopropyl myristate | 10.0 |
| 10. Antioxidant | suitable amount |
| 11. Perfume | suitable amount |

<Method>

The above component 1 was added to a part of the component 7, and these were kneaded by a roller. A mixture obtained by mixing the other components and heat-dissolving the same was added thereto, and they were uniformly dispersed using a homomixer. This dispersion was poured into a lipstick mold, and quenched rapidly to obtain a desired lip cream.

In the lip cream of Example 3, the color was changed from reddish purple to red according to a viewing angle after it was put on the lips. Thus, the interference color clearly arises from the composite powder of the present invention. Besides, the dull tone of the lips was concealed with this interference color, clearly improving the color of the lips. Further, it was excellent in the slipperiness in coating, so that the coating could easily be conducted.

EXAMPLE 4
Hair gel:

| Components | Amount (parts by weight) |
|---|---|
| 1. Carboxyvinyl polymer | 0.7 |
| 2. Polyvinylpyrrolidone | 2.0 |
| 3. Glycerin | 0.2 |
| 4. Sodium hydroxide | 0.1 |
| 5. Ethyl alcohol | 20.0 |
| 6. Invention composite powder (1) | 2.0 |
| 7. Polyoxyethylene octyl dodecyl ether | 0.2 |
| 8. Deionized water | 74.8 |
| 9. Chelating agent | suitable amount |
| 10. Perfume | suitable amount |

<Method>

The above-mentioned component 1 was dispersed in the component 3 and a part of the component 8. The other components were added to the remaining part of the component 8, and these were mixed while being stirred. The above-mentioned dispersion was added thereto, and the mixture was stirred to obtain a desired hair gel.

The hair gel of Example 4 was not sticky, and there was observed an effect that the hair color after coating the same looked radish brown.

EXAMPLE 5
Powdery foundation:

| Components | Amount (parts by weight) |
|---|---|
| 1. Invention composite powder (1) | 16.0 |
| 2. Talc | 21.2 |
| 3. White mica | 50.0 |
| 4. Red iron oxide | 0.7 |
| 5. Yellow iron oxide | 1.0 |
| 6. Black iron oxide | 0.1 |
| 7. Dimethylpolysiloxane | 1.0 |
| 8. Cetyl 2-ethylhexanoate | 9.0 |
| 9. Sorbitan sesquioleate | 1.0 |
| 10. Paraben | suitable amount |
| 11. Perfume | suitable amount |

<Method>

The above-mentioned components 1 to 6 were mixed using a Henschel mixer, and a mixture obtained by heat-dissolving the components 7 to 11 was added thereto. The resulting mixture was pulverized, and shaped in a dish to obtain a desired powdery foundation.

The powdery foundation of Example 5 was lightly spread, and was observed to have an effect of beautifully improving the skin color with the function of the pigment color and the interference color generated from the composite powder of the present invention.

EXAMPLE 6
Emulsified foundation:

| Components | Amount (parts by weight) |
|---|---|
| 1. Sericite | 5.36 |
| 2. Kaolin | 4.0 |
| 3. Invention composite powder (1) | 9.32 |
| 4. Red iron oxide | 0.36 |
| 5. Yellow iron oxide | 0.8 |

-continued

| Components | Amount (parts by weight) |
|---|---|
| 6. Black iron oxide | 0.16 |
| 7. Liquid paraffin | 5.0 |
| 8. Decamethylcyclopentasiloxane | 12.0 |
| 9. Polyoxyethylene-modified silicone | 4.0 |
| 10. 1,3-Butylene glycol | 5.0 |
| 11. Deionized water | 54.0 |
| 12. Paraben | suitable amount |
| 13. Perfume | suitable amount |

<Method>

The above-mentioned components 10 to 12 were heat-stirred, and the components 1 to 6 were then added thereto. The mixture was treated at 70° C. using a homomixer. Further, the components 7 to 9 and 13 were mixed at 70° C., and added to the homomixer-treated product. Further, the treatment was conducted with the homomixer at 70° C. The resulting product was cooled while being stirred to obtain a desired emulsified foundation.

The emulsified foundation of this Example 6 was lightly spread, and was observed to have the effect of beautifully improving the skin color.

EXAMPLE 7
Eye shadow:

| Components | Amount (parts by weight) |
|---|---|
| 1. Talc | 40.0 |
| 2. Mica | 15.0 |
| 3. Sericite | 5.0 |
| 4. Invention composite powder (2) | 25.0 |
| 5. Liquid paraffin | 6.0 |
| 6. Dimethylpolysiloxane | 2.0 |
| 7. Sorbitan sesquioleate | 5.0 |
| 8. Decamethylcyclopentasiloxane | 2.0 |
| 9. Paraben | suitable amount |
| 10. Antioxidant | suitable amount |
| 11. Perfume | suitable amount |

<Method>

The above-mentioned components 1 to 4 and 9 were mixed using a stirrer, and a mixture obtained by uniformly mixing the remaining components was added thereto. The resulting mixture was treated with a mill, and compression-molded to obtain a desired eye shadow.

The eye shadow of this Example 7 was excellent in the touch in coating, and also excellent in the appearance after coating the same.

EXAMPLE 8
Paint composition:

| Components | Amount (parts by weight) |
|---|---|
| 1. Thermoplastic acrylic resin | 90.0 |
| 2. Invention composite powder (1) | 10.0 |
| 3. Toluene | 10.0 |

<Method>

The thermoplastic acrylic resin and Invention composite powder (1) were mixed, and the mixture was then diluted with toluene to obtain a paint composition.

The paint composition of this Example 8 was coated on a soft steel plate 0.8 mm thick to a film thickness of from 30 to 35 μm using a bar coater, allowed to stand at room temperature for 10 minutes, and baked at 80° C. for 20 minutes. The resulting coated film had a pale red interference color. Further, this coated film had the (L* a* b*) value of (24.34 8.75 −14.29).

EXAMPLE 9
Plastic colored product:

| Components | Amount (parts by weight) |
|---|---|
| 1. Invention composite powder (2) | 60.0 |
| 2. Polyethylene resin | 40.0 |

<Method>

The above-mentioned components were pelletized using a kneader to obtain a plastic colored product.

The resulting plastic colored product had a pale green interference color. Further, this plastic colored product had the (L* a* b*) value of (28.80 −3.88 −3.28).

EXAMPLE 10
Coating sticky sheet:

| Components | Amount (parts by weight) |
|---|---|
| 1. Acrylic tackifier (Oribine BPS (trademark) - 1109 supplied by Toyo Ink) | 100.0 |
| 2. Curing agent (Oribine BPS (trademark) - 8515 supplied by Toyo Ink) | 2.0 |
| 3. Invention composite powder (4) | 10.0 |

<Method>

The above-mentioned components were mixed, and the mixture was coated on a polyester sheet (thickness 50 μm) to a film thickness of 30 μm (after drying), and dried. Subsequently, a peel-off liner was stuck thereto to obtain a coating sticky sheet.

The thus-obtained coating sticky sheet had a pale blue interference color. Further, this sheet had the (L* a* b*) value of (25.41 −1.72 −11.29).

EXAMPLE 11
Printing ink composition:

| Components | Amount (parts by weight) |
|---|---|
| 1. Invention composite powder (2) | 14.0 |
| 2. Ethylene-vinyl acetate copolymer resin | 7.2 |
| 3. Polypropylene chloride | 5.8 |
| 4. Toluene | 58.0 |
| 5. Ethyl acetate | 11.0 |
| 6. Isopropyl alcohol | 3.0 |
| 7. Polyethylene wax | 0.8 |
| 8. Antistatic agent | 0.2 |

<Method>

The above-mentioned components were mixed, and kneaded using a sand mill to obtain a printing ink composition.

A black sheet was printed with a film thickness of 60 μm (after drying) using the printing ink composition of this Example 11. Then, the coated product had a pale green interference color. Further, this coated product had the (L* a* b*) value of (28.29 −5.99 −2.01).

EXAMPLE 12
Printing ink composition:

| Components | Amount (parts by weight) |
|---|---|
| 1. Invention composite powder (3) | 15.0 |
| 2. Acrylic resin | 20.0 |
| 3. Naphtha | 35.0 |
| 4. Butyl cellosolve | 30.0 |

<Method>

The above-mentioned components were mixed, and kneaded using a sand mill to obtain a printing ink composition.

A black sheet was printed with a film thickness of 50 μm (after drying) using the printing ink composition of this Example 12. Then, the coated product had a pale yellow interference color. Further, this coated product had the (L* a* b*) value of (24.83 5.05 5.66).

EXAMPLE 13

Light diffusion plate for liquid crystal display:

| Components | Amount (parts by weight) |
|---|---|
| 1. Invention composite powder (1) | 1.0 |
| 2. Nitrocellulose lacquer | 15.0 |

<Method>

The above-mentioned components were mixed, and the mixture was coated on a polycarbonate film to a film thickness of 200 μm (in drying) using a bar coater.

The resulting film was incorporated between a back light (illumination) and a liquid crystal layer of a liquid crystal display to diffuse light from the back light. Thus, it could be used as a light diffusion plate for supplementing a color of the display. Further, this diffusion plate had the (L* a* b*) value of (20.83 5.53 −10.44).

What is claimed is:

1. A composite powder comprising a plurality of composite powder particles, the composite powder particle comprising a spherical core particle having a refractive index of from 1.40–1.60, and a diameter of about 2.0–50.0 μm, and a coating component which is coated in film form on the surface of the core particle and has a refractive index of from 2.00–2.90 the diameters of the composite powder particles being distributed in a ratio of at least 60% in terms of a volume distribution within the range of (X+3)μm wherein X μm is an average diameter of the composite powder particles, whereby the composite powder applied on a substrate produces an interference color.

2. The composite powder of claim 1, wherein the diameters of the composite powder particles are distributed in a ratio of at least 70% in terms of a volume distribution within the range of (X+3)μm wherein X μm is an average diameter of the composite powder particles.

3. The composite powder of claim 1, wherein the coating component has an optical film thickness of between 190 and 780 nm.

4. The composite powder of claim 1, wherein the core particle is made of a material selected from the group consisting of silicon dioxide, alumina, calcium carbonate, barium sulfate, nylon, polyethylene, polystyrene, and polymethyl methacrylate.

5. The composite powder of claim 1, wherein the coating component is selected from the group consisting of titanium dioxide, titanium oxide having a lower rate of titanium oxidation than titanium dioxide, zinc oxide, zironium oxide, and iron oxide.

6. The composite powder of claim 1, wherein the coating component is titanium dioxide, which powder is produced by a method in which hydrous titanium dioxide is precipitated on a surface of a core particle in an aqueous solution of a titanium inorganic acid salt and then heated in an ambient atmosphere.

7. The composite powder of claim 1, wherein the coating component is titanium dioxide, which powder is produced by a method in which while titanium alkoxide is contacted with a core particle in a solvent, the titanium alkoxide is hydrolyzed and burned.

8. The composite powder of claim 1, wherein the core particle is made of silicon dioxide and the coating component is titanium dioxide.

9. The composite powder of claim 8, wherein the coating component/core particle weight ratio is in the range of from 0.09 to 1.25.

10. The composite powder of claim 8, wherein the coating component/core particle weight ratio is in the range of from 0.4 to 1.0.

11. A method of use of the composite powder of claim 1, wherein the composite powder is applied on a substrate to form a composite powder layer, whereby light interference caused in the composite powder layer results in an interference color.

12. A coloring composition containing the composite powder of claim 1.

13. The coloring composition of claim 12, which is an external composition.

14. The coloring composition of claim 13, wherein the external composition is a makeup product.

15. The coloring composition of claim 13, which contains 0.1 to 90.0% by weight of the composite powder.

16. The coloring composition of claim 12, which is a paint composition.

17. The coloring composition of claim 12, which is a printing ink composition.

18. The coloring composition of claim 12, which is a sticky composition.

19. The coloring composition of claim 18, which contains at least 1.0% by weight of the composite powder.

20. A method of use of the coloring composition of claim 12, wherein the coloring composition is applied on a substrate to form a composite powder layer, whereby light interference caused in the composite powder layer results in an interference color.

* * * * *

UNITED STATES PATENT AND TRADEMARK OFFICE
CERTIFICATE OF CORRECTION

PATENT NO. : 6,207,174 B1
DATED : March 27, 2001
INVENTOR(S) : Teruhiko Hineno et al.

It is certified that error appears in the above-identified patent and that said Letters Patent is hereby corrected as shown below:

Title page,
Item [54], should read -- COMPOSITE POWDER AND COLORING COMPOSITION CONTAINING THE SAME --.

Signed and Sealed this

Eighth Day of January, 2002

*Attest:*

JAMES E. ROGAN
*Attesting Officer*    *Director of the United States Patent and Trademark Office*